(12) United States Patent
Lee et al.

(10) Patent No.: US 8,232,318 B2
(45) Date of Patent: Jul. 31, 2012

(54) APPROACHES TO TREAT CANCER USING HB-EGF INHIBITORS

(75) Inventors: Sam W. Lee, Newton, MA (US); Anna Mandinova, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 12/847,509

(22) Filed: Jul. 30, 2010

(65) Prior Publication Data

US 2011/0060047 A1    Mar. 10, 2011

Related U.S. Application Data

(60) Provisional application No. 61/230,432, filed on Jul. 31, 2009.

(51) Int. Cl.
*A61K 31/192*   (2006.01)
*A61P 35/00*    (2006.01)
*C12N 5/02*     (2006.01)

(52) U.S. Cl. ........................ 514/568; 435/375

(58) Field of Classification Search ............ None
See application file for complete search history.

(56) References Cited

FOREIGN PATENT DOCUMENTS

| | | | |
|---|---|---|---|
| JP | 2005029571 | * | 2/2005 |
| WO | WO 2008/013062 | | 1/2008 |

OTHER PUBLICATIONS

Dorwald (Side Reactions in Organic Synthesis: A guide to successful synthesis design, Weinheim: WILEY-VCH, Verlag GmbH & Co. KGaA, 2005, Preface).*
Nicholson et al. EGFR and cancer prognosis. European Journal of Cancer, 37, 2001, S9-S15.*
English translation, JP 200502957, 2005.*
Mizushina, et al.; "Novel anti-inflammatory compounds from Myrsine seguinii, terpeno-benzoic acids, are inhibitors of mammalian DNA polymerases"; Biochemica et Biophysica Acta; 2000; 1475(1): 1-4.
Hirota, et al.; "Myrsinoic Acids B, C and F, Anti-inflammatory Compounds from Myrsine seguinii"; Biosci. Biotechnol. Biochem., 2002; 66(3): 655-659.
Makabe, et al.; "Myrsinoic Acid E, an Anti-inflammatory Compound from Myrsine seguinii"; Biosci. Biotechnol. Biochem.; 2003; 67(9): 2038-2041.
Okayama, et al., "*Identification of Genes Upregulated in ALK-Positive and EGFR/KRAS/ALK-Negative Lung Adenocarcinomas*", Cancer Res 2012;72:100-111. Published OnlineFirst Nov. 11, 2011; access article at doi:10.1158/0008-5472.CAN-11-1403.
Lorusso et al., "*Which role for EGFR therapy in breast cancer?*", Front Biosci (Schol Ed.) 2012;4:31-42.
Yamatodani et al., "*Epidermal growth factor receptor status and persistent activation of Akt and p44/42 MAPK pathways correlate with the effect of cetuximab in head and neck and colon cancer cell lines*", J. Cancer Res. Clin. Oncol., 2009; 135(3):395-402. Epub Sep. 24, 2008.

* cited by examiner

*Primary Examiner* — Brandon Fetterolf
*Assistant Examiner* — Anna Pagonakis
(74) *Attorney, Agent, or Firm* — Fish & Richardson P.C.

(57) ABSTRACT

The invention provides methods for the treatment of cancer in a subject by the administration of myrsinoic acid A and/or one or more myrsinoic acid A analogs.

16 Claims, 14 Drawing Sheets

APPROACHES TO TREAT CANCER USING HB-EGF INHIBITORS

RELATED APPLICATIONS

This application claims the benefit under 35 U.S.C. §119 (e) of U.S. provisional application Ser. No. 61/230,432, filed Jul. 31, 2009, the disclosure of which is incorporated by reference herein in its entirety.

FIELD OF THE INVENTION

The invention provides methods for the treatment of cancer in a subject by the administration of myrsinoic acid A and/or one or more myrsinoic acid A analogs.

BACKGROUND OF THE INVENTION

Cancer development is a multistage process that results from the step-wise acquisition of genetic alterations. These alterations may involve the dysregulation of a variety of normal cellular functions, leading to the initiation and progression of cancer cells. Cancer cells bear an indefinite proliferative capacity and are able to elude the commitment to terminal differentiation and quiescence that regulates normal tissue homeostasis.

The human epidermal growth factor receptor (HER/ErbB) family consists of the receptors EGFR (ErbB1), HER2 (ErbB2), HER3(ErbB3) and HER4 (ErbB4). The receptors can activate numerous downstream signaling pathways in response to extracellular ligands and regulate diverse cellular processes including differentiation, migration, proliferation, and survival. Members of the epidermal growth factor receptor family are over-expressed in many types of human cancers (e.g., Normanno et al., 2006, Gene 366, 2-16). In addition, mutational activation of members of the EGFR family has been observed in a variety of human malignancies (e.g., Charpidou et al., 2008, In vivo 22: 529-536). Suppressing the activity of EGFR receptors, for instance through the administration of receptor tyrosine kinase inhibitors, has provided new methods of anti-cancer therapy.

Heparin-Binding Epidermal Growth Factor-like growth factor (HB-EGF) is a ligand for the EGFR family of receptors that can bind and activate all members of the EGFR family of receptors (See e.g., Elenius et al., 1997, EMBO J 16:1268-1278; Johnson et al., 2005, J Cell Physiol 205:218-227). While there are a variety of ligands that can activate members of the EGFR family of receptors, only HB-EGF is abundantly expressed in many types of cancers including ovarian, gastric, pancreatic, renal, lung, prostate, and breast cancer, melanoma and glioblastoma. HB-EGF has also been shown to play a key role in the acquisition of malignant phenotypes, such as cell survival, peritoneal fluid, cell adhesion on extracellular matrices, invasion, angiogenesis, tumorigenicity and chemoresistance in cancer (Ongusaha et al., 2004, Cancer Res 64: 5283).

SUMMARY OF THE INVENTION

In one aspect, the invention provides methods for the treatment of cancer in a subject. In some embodiments, the methods for treating a cancer in a subject comprise administering to a subject in need of such treatment a therapeutically effective amount of a composition comprising myrsinoic acid A and/or one or more myrsinoic acid A analogs to treat the cancer in the subject. In some embodiments, the treatment suppresses further growth of the cancer. In some embodiments, the treatment results in regression of the cancer. In some embodiments, the cancer is characterized by cells having increased Epidermal Growth Factor Receptor signaling. In some embodiments, the cancer is characterized by cells over-expressing Heparin-Binding Epidermal Growth Factor-like growth factor (HB-EGF). In some embodiments, the cancer is unresponsive to treatment by one or more Epidermal Growth Factor Receptor tyrosine kinase inhibitors. In some embodiments, the subject is otherwise free of symptoms treatable by myrsinoic acid A and/or one or more myrsinoic acid A analogs.

In one aspect, the invention provides a method for suppressing the growth of a cell, the method comprising contacting the cell with a composition comprising myrsinoic acid A and/or one or more myrsinoic acid A analogs to suppress the growth of the cell. In some embodiments, the cell has an increased Epidermal Growth Factor Receptor signaling. In some embodiments, the cell over-expresses Heparin-Binding Epidermal Growth Factor-like growth factor (HB-EGF). In some embodiments, the cell is a cancer cell. In some embodiments, the cell is in a subject.

In one aspect, the invention provides a method for suppressing Epidermal Growth Factor Receptor (EGFR) signaling in a cell, the method comprising contacting the cell with a composition comprising myrsinoic acid A and/or one or more myrsinoic acid A analogs to suppress EGFR signaling in the cell. In some embodiments, the cell has increased Epidermal Growth Factor Receptor signaling. In some embodiments, the cell over-expresses Heparin-Binding Epidermal Growth Factor-like growth factor (HB-EGF). In some embodiments, the cell is a cancer cell. In some embodiments, the cell is in a subject.

In one aspect, the invention provides a pharmaceutical composition comprising myrsinoic acid A and/or one or more myrsinoic acid A analogs and a pharmaceutically acceptable carrier. In some embodiments, the pharmaceutical composition further comprises one or more non-myrsinoic acid A anti-cancer compounds.

In one aspect, the invention provides a kit comprising a pharmaceutical composition comprising a therapeutically effective amount of myrsinoic acid A and/or one or more myrsinoic acid A analogs, and instructions for preparation and/or administration of the pharmaceutical composition. In some embodiments, the kit further comprises a pharmaceutically acceptable carrier. In some embodiments, the kit further comprises one or more non-myrsinoic acid A anti-cancer compounds.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including", "comprising", "having", "containing", "involving", and variations thereof herein, is meant to encompass the items listed thereafter and equivalents thereof as well as additional items.

BRIEF DESCRIPTION OF THE DRAWINGS

The figures are illustrative only and are not required for enablement of the invention disclosed herein.

DETAILED DESCRIPTION OF THE INVENTION

Figure 1:
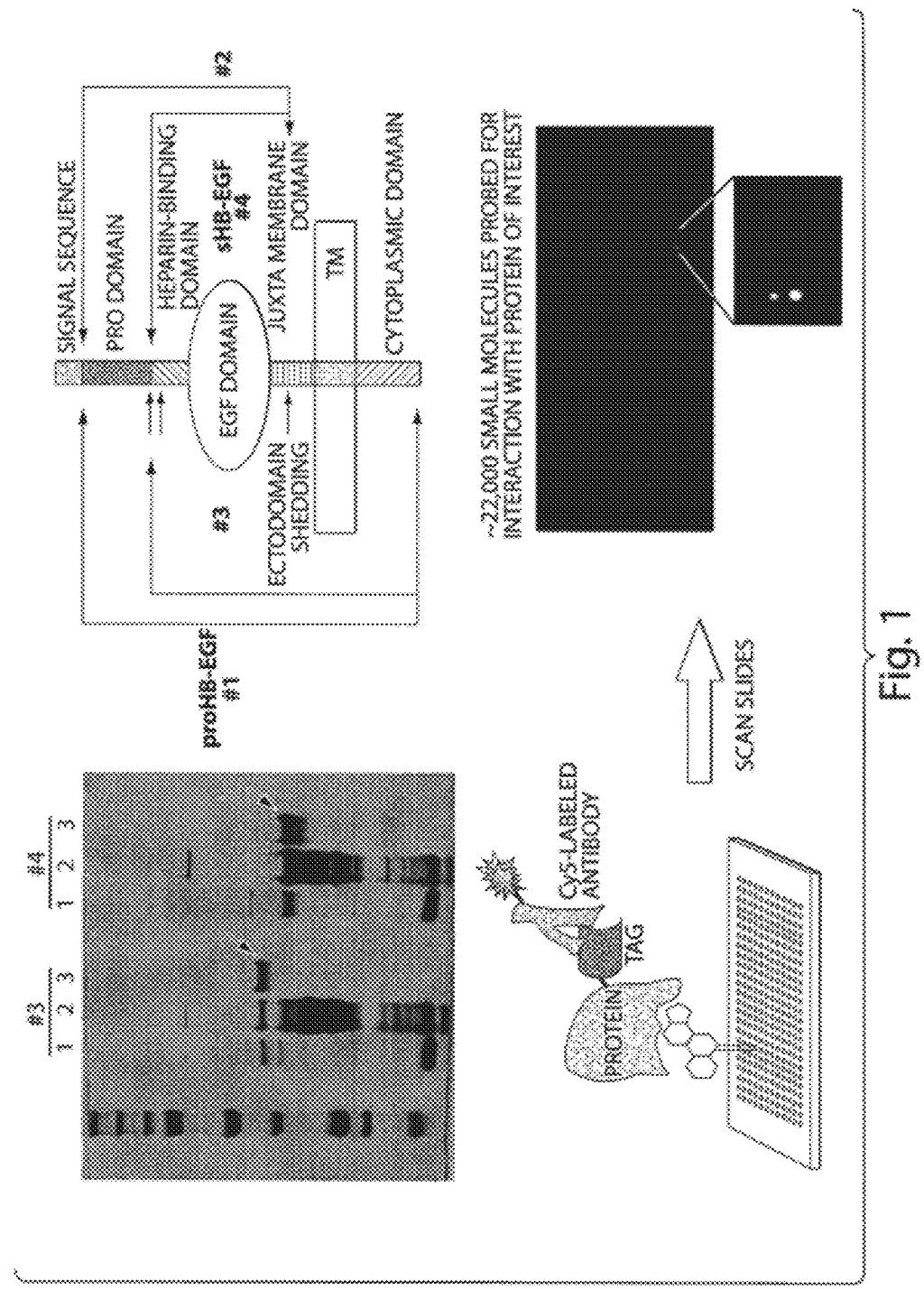
FIG. 1 shows an overview of the screening of compounds for binding to HB-EGF using small molecule microarrays.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

In one aspect, the invention provides methods for the treatment of cancer in a subject. In some embodiments, the methods for treating a cancer in a subject comprise administering to a subject in need of such treatment a therapeutically effective amount of a composition comprising myrsinoic acid A and/or one or more myrsinoic acid A analogs to treat the cancer in the subject.

In one aspect the invention provides methods for suppressing the growth of a cell. In some embodiments, the cell is a cancer cell. In some embodiments, the cell is in a subject. In some embodiments, the methods for suppressing the growth of a cell comprise contacting the cell with a composition comprising myrsinoic acid A and/or one or more myrsinoic acid A analogs to suppress the growth of the cell.

Cancer cells are often characterized by increased intracellular signaling which can result in the uncontrolled growth of the cancer cell. Increased intracellular signaling can be caused by a variety of factors including increased expression, activity or availability of cellular receptors, increased expression, activity or availability of downstream signaling elements, or the increased expression, activity or availability of activating ligands. Increased intracellular signaling can also be caused by mutations in ligands, receptors or downstream elements, etc., that result in an increase in functionality of the ligand, receptor or downstream element. Alternatively, or additionally, increased signaling can be caused by the inactivation or suppression in expression of negative regulators of intracellular signaling pathways.

One method of cancer therapy is afforded through the suppression of the growth of cancer cells with increased intracellular signaling. The growth of such cancer cells can be suppressed by suppressing intracellular signaling pathways of these cells. Cancer cells have often become dependent on specific intracellular signaling pathways whose activity has been increased. In some cases, increased intracellular activity is acquired through mutations in a receptor, such as the Epidermal Growth Factor Receptor (EGFR). Because normal (healthy) cells do not have this increased intracellular signaling, cancer cells can be specifically therapeutically targeted. Suppression of intracellular signaling can be achieved by intervening with any part of the signaling pathway, including preventing or suppressing the functionality of any of the elements in the signaling pathway, for instance by preventing or suppressing the interaction between a ligand and its receptor, the interaction between a receptor and a co-factor or co-receptor required for activation, the interaction between a receptor and its downstream elements, or the interaction between the various downstream elements.

In one aspect, the invention provides methods for the treatment of cancer in a subject. In some embodiments, the cancer is characterized by cells having increased intracellular signaling. In some embodiments, the cancer is characterized by cells having increased Epidermal Growth Factor Receptor signaling. In some embodiments, the cancer is characterized by cells over-expressing Heparin-Binding Epidermal Growth Factor-like growth factor (HB-EGF).

In one aspect, the invention provides methods for suppressing the growth of a cell. In one aspect, the invention provides methods for suppressing Epidermal Growth Factor Receptor (EGFR) signaling in a cell. In some embodiments, the cell has increased Epidermal Growth Factor Receptor signaling. In some embodiments, the cell over-expresses Heparin-Binding Epidermal Growth Factor-like growth factor (HB-EGF).

A pathway with increased intracellular signaling in a variety of cancers is the EGFR signaling pathway. EGFR signaling is initiated by stimulation of one or more of the cellular receptors EGFR (ErbB1), HER2 (ErbB2), HER3 (ErbB3) and HER4 (ErbB4), that make up the human epidermal growth factor receptor (HER/ErbB) family of proteins. Activation of these receptors results in the activation of a variety of downstream pathways including the activation of proteins involved in proliferation, cell cycle progression and metastasis. EGFR signaling is initiated predominantly through receptor pairs comprising EGFR (ErbB1) as one of the entities (e.g., EGFR-EGFR, EGFR-HER2, EGFR-HER3). However, alternative combinations of receptors without EGFR (e.g., HER2-HER3) have also been found to activate EGFR signaling.

EGFR receptors can be activated through interaction with ligands. These ligands can be found in the cellular environment and can be produced by surrounding cells or produced by the cell itself. Some ligands are specific for a particular receptor in the EGFR family while other ligands are promiscuous and can interact with more than one EGFR receptor. Preventing one or more ligands from binding to the EGFR receptors provides a method for suppressing EGFR signaling. Heparin-Binding Epidermal Growth Factor-like growth factor (HB-EGF) is a ligand that can bind any receptor in the EGFR family and that can thereby stimulate any EGFR receptor or combination of EGFR receptors. HB-EGF can be produced as a membrane-anchored form (pro-HB-EGF) and is processed to a soluble form (s-HB-EGF). HB-EGF has been shown to stimulate a variety of cells, both in autocrine or paracrine fashion. In addition, HB-EGF is over-expressed in a variety of tumors when compared to normal tissue (Ongusaha et al., 2004, Cancer Research 64: 5283-5290).

In one aspect, the invention provides methods for the treatment of cancer in a subject. In some embodiments, the cancer is treated by suppressing or inhibiting the interaction between HB-EGF and an EGFR receptor. In some embodiments, the compound that suppresses or inhibits the interaction between HB-EGF and an EGFR receptor is myrsinoic acid A or a myrsinoic acid A analog.

In one aspect, the invention provides methods for suppressing the growth of a cell. In one aspect, the invention provides methods for suppressing Epidermal Growth Factor Receptor (EGFR) signaling in a cell. In some embodiments, the growth of a cell and/or EGFR signaling in a cell is suppressed by suppressing or inhibiting the interaction between HB-EGF and an EGFR receptor. In some embodiments, the growth of a cell and/or EGFR signaling in a cell is suppressed by contacting the cell with a compound that suppresses or inhibits the interaction between HB-EGF and an EGFR receptor. In some embodiments, the compound that suppresses or inhibits the interaction between HB-EGF and an EGFR receptor is myrsinoic acid A or a myrsinoic acid A analog.

In one aspect the invention provides methods for the treatment of cancer in a subject, wherein the cancer is unresponsive to treatment by one or more Epidermal Growth Factor Receptor tyrosine kinase inhibitors.

In general, EGFR signaling is initiated by the activation of the combination of two receptors in the EGFR receptor family, one of which is EGFR (ErbB1). Epidermal Growth Factor Receptor tyrosine kinase inhibitors can prevent the EGFR receptor combination from activating the downstream signaling pathway by inhibiting or suppressing the kinase function of the EGFR (ErbB1) receptor. Tyrosine kinase inhibitors have been found to be effective against a number of cancers that depend on EGFR signaling for growth, such as cancers that have a consistently active EGFR receptor and/or that have increased EGFR signaling (e.g., through over-expression of the receptor). However, a number of these cancers that initially respond to treatment by the tyrosine kinase inhibitors ultimately become resistant to these inhibitors because they are able to use, or evolve to be able to use, an alternative combination of receptors in the EGFR family to stimulate the EGFR pathway, such as the combination of Her2 and Her3 (See e.g., Kong et al., 2008 PLoS One 3, e2881). Because the cancer cells no longer depend the EGFR (ErbB1) receptor to survive, the cancer becomes resistant to EFGR receptor inhibitors.

The methods presented in the instant invention circumvent and overcome the problem of the acquired resistance of EGFR dependent cancer cells to tyrosine kinase inhibitors. By inhibiting or suppressing the interaction of the HB-EGF ligand, which can stimulate all EGFR receptors, with an EGFR receptor, the stimulation of all EGFR signaling can be inhibited or suppressed regardless of the EGFR receptor, or combination of EGFR receptors, that activates the EGFR signaling pathway. In some embodiments, the compound that suppresses or inhibits the interaction between HB-EGF and an EGFR receptor is myrsinoic acid A or a myrsinoic acid A analog.

Figure 3:
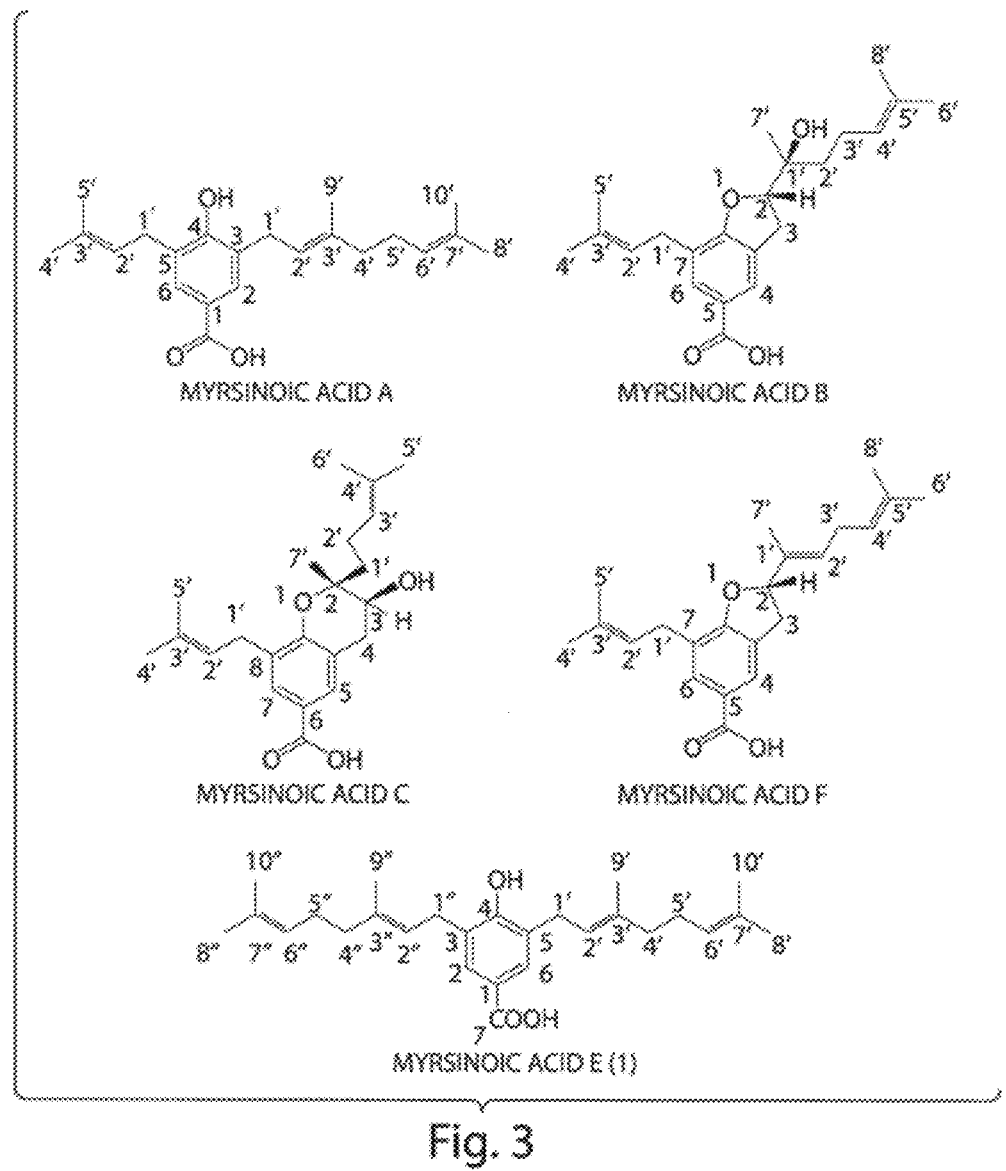
FIG. 3 shows the structures of myrsinoic acid A, B, C, E and F.

Myrsinoic acids have been isolated from plants from the myrsine family, which is found worldwide in tropical and subtropical areas. The first myrsinoic acid compound to be isolated from plants of the myrsine family was myrsinoic acid A (3-geranyl-4-hydroxy-5-(3'-methyl-2'butenyl)-benzoic acid; also referred to herein as NP2008; Dong et al. 1999, Biosci. Biotechnol. Biochem 63: 1650-1653). In addition to myrsinoic acid A, four related myrsinoic acid compounds have been isolated: myrsinoic acid B, C, E and F (Hirota et al. 2002, Biosci. Biotechnol. Biochem, 66: 655-659; Makabe et al. 2003, Biosci. Biotechnol. Biochem 67: 2038-2041). The structures of the myrsinoic acids A, B, C, E and F is shown in FIG. 3.

Myrsinoic acids A, B, C, E and F have been shown to act as anti-inflammatory compounds in a mouse ear inflammatory test (Dong et al. 1999, Biosci. Biotechnol. Biochem 63: 1650-1653; Hirota et al. 2002, Biosci. Biotechnol. Biochem, 66: 655-659; Makabe et al. 2003, Biosci. Biotechnol. Biochem 67: 2038-2041). Of these myrsinoic acids, myrsinoic acid F was identified as the most potent anti-inflammatory compound (Hirota et al. 2002, Biosci. Biotechnol. Biochem, 66: 655-659). In addition, myrsinoic acid A has also been shown to act as an inhibitor of some DNA polymerases, while myrsionic acid B has been identified as a methioninase inhibitor (Mizushima et al. 2000 Biochem Biophys Acta, 1475: 1-4; Ito et al. Biosci Biotechnol Biochem. 2008, 72: 2411-4). It has been shown that replacing the hydrogen at either the acidic position or the 4'hydroxy position of myrsinoic acid A result in the suppression of both the anti-inflammatory activity and the DNA polymerase inhibitor activity of myrsinoic acid A (Mizushima et al. 2000 Biochem Biophys Acta, 1475: 1-4).

The invention also embraces myrsinoic acid A analogs. Myrsinoic acid A analogs are chemically modified versions of myrsinoic acid A. In some embodiments, the myrsinoic acid A analogs have one or more myrsinoic acid A activities (as described herein), e.g., anti-cancer activity. The one or more activities are preferably present in the myrsinoic acid A analogs in significant amounts, e.g., at greater than 10%, 20%, 30%, 40%, 50%, 60%, 70%, 80%, or 90% of the activity of myrsinoic acid A, respectively. More preferably, the one or more activities are preferably present in the myrsinoic acid A analogs at greater than 100%, 110%, 120%, 130%, 140%, 150%, 160%, 170%, 180%, 190%, 200%, or more, of the activity of myrsinoic acid A. The myrsinoic acid A analogs may not have all of the activities of myrsinoic acid A. However, non-active myrsinoic acid A analogs, having none of the activities of myrsinoic acid A in significant amounts, are not useful in the methods of the invention.

The invention also embraces prodrugs of myrsinoic acid A and myrsinoic acid A analogs. Prodrugs of myrsinoic acid A and myrsinoic acid A analogs are modified versions of myrsinoic acid A and myrsinoic acid A analogs that may have improved stability and/or handling properties compared to the unmodified version of myrsinoic acid A and myrsinoic acid A analogs. Prodrugs of myrsinoic acid A and myrsinoic acid A analogs are metabolized in vivo to result in myrsinoic acid A and myrsinoic acid A analogs, respectively.

Myrsinoic acid A, analogs of myrsinoic acid A and prodrugs of myrsinoic acid A and prodrugs of analogs of myrsinoic acids A are also referred to herein as the compounds of the invention.

It should be appreciated that whenever the invention refers to methods of administration of myrsinoic acid A or analogs of myrsinoic acid A, or methods of contacting a cell with myrsinoic acid A or analogs of myrsinoic acid A, the invention also encompasses the administration of, or contacting of cells with, prodrugs of myrsinoic acid A or prodrugs of analogs of myrsinoic acid A.

Treating a Cancer in a Subject

In one aspect, the invention provides methods for treating a cancer in a subject by administering to a subject in need of such treatment a therapeutically effective amount of a composition comprising myrsinoic acid A and/or one or more myrsinoic acid A analogs to treat the cancer in the subject. As used herein, "treating a cancer" includes, but is not limited to, preventing or reducing the development of a cancer, reducing the symptoms of cancer, suppressing or inhibiting the growth of an established cancer, preventing metastasis and/or invasion of an existing cancer, promoting or inducing regression of the cancer, inhibiting or suppressing the proliferation of cancerous cells, reducing angiogenesis or increasing the amount of apoptotic cancer cells. In some embodiments, the compounds of the invention are administered to a subject at risk of developing a cancer for the purpose of reducing the risk of developing the cancer.

In some embodiments, the invention provides methods for treating a specific cancer. In some embodiments, the invention provides methods for treating a cancer characterized by cells having increased Epidermal Growth Factor Receptor signaling (EGFR signaling). In some embodiments, the invention provides methods for treating a cancer characterized by cells over-expressing Heparin-Binding Epidermal Growth Factor-like growth factor (HB-EGF). In some embodiments, the invention provides methods for treating a cancer that is unresponsive to treatment by one or more Epidermal Growth Factor tyrosine kinase inhibitors.

Subject

In one aspect, the invention provides methods for the treatment of cancer in a subject. A "subject", as used herein, is a human or other vertebrate mammal including, but not limited to, mouse, rat, dog, cat, horse, cow, pig, sheep, goat, or non-human primate.

A "subject in need of treatment", as used herein, means a subject that is identified as being in need of treatment. For instance, a subject in need of cancer treatment is a subject identified as having cancer or being at risk for developing cancer. A subject may be diagnosed as being in need of treatment by a healthcare professional and/or by performing one or more diagnostic assays. For instance, a subject in need of cancer treatment may be a subject diagnosed with cancer or being at risk of cancer by a healthcare professional. Diagnostic assays to evaluate if a subject has a cancer or is at risk for developing cancer are known in the art.

In some embodiments, the subject to be administered a therapeutically effective amount of a composition comprising myrsinoic acid A and/or one or more myrsinoic acid A analogs is otherwise free of symptoms treatable by myrsinoic acid A and/or one or more myrsinoic acid A analogs. In some embodiments, the subject to be administered a therapeutically effective amount of composition comprising myrsinoic acid A and/or one or more myrsinoic acid A analogs is otherwise free of symptoms treatable by an anti-inflammatory compound.

Cancer

In one aspect, the invention provides methods for the treatment of cancer. "Cancer", as used herein, refers to an uncontrolled growth of cells which interferes with the normal functioning of the bodily organs and systems. Cancers, including those cancers which migrate from their original location and seed vital organs, can eventually lead to the death of the subject through the functional deterioration of the affected organs. Cancers can be classified into a variety of categories including, carcinomas, sarcomas and hematopoietic cancers. Carcinomas are malignant cancers that arise from epithelial cells and include adenocarcinoma and squamous cell carcinoma. Sarcomas are cancer of the connective or supportive tissue and include osteosarcoma, chondrosarcoma and gastrointestinal stromal tumor. Hematopoietic cancers, such as leukemia, are able to outcompete the normal hematopoietic compartments in a subject, thereby leading to hematopoietic failure (in the form of anemia, thrombocytopenia and neutropenia) ultimately causing death. A person of ordinary skill in the art can classify a cancer as a sarcoma, carcinoma, hematopoietic cancer or a different category.

Cancer, as used herein, includes the following types of cancer, breast cancer, biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will be known to one of ordinary skill in the art.

A cancer "characterized by cells having increased Epidermal Growth Factor Receptor signaling" (EGFR signaling), is a cancer comprising cancer cells that have increased EGFR signaling. The cancer can consist exclusively of cells that have increased EGFR signaling or the cancer may include a subpopulation of cells that have increased EGFR signaling. Cells having "increased EGFR signaling" are cells that have increased EGFR signaling compared to wild-type ("normal" or "non-cancerous") cells. Increased EGFR signaling can be caused, for instance, by activating mutations in one or more EGFR receptors or other proteins in the EGFR signaling pathway, or by overexpression of one or more EGFR receptors or other proteins in the EGFR signaling pathway. Cells with increased EGFR signaling can be identified, for example, by assaying the levels and/or activation status of the EGFR receptors or other proteins in the signaling pathway. Assays that can detect the level or activation status of proteins are known in the art and include western blots and protein array analysis. Increased intracellular signaling, as compared to wild-type cells, includes 1% or more, 5% or more, 10% or more, 20% or more, 50% or more, 100% or more, 5× or more, 10× or more, 100× or more, 1000× or more intracellular signaling.

A cancer "characterized by cells over-expressing Heparin-Binding Epidermal Growth Factor-like growth factor (HB-EGF)", is a cancer comprising cancer cells that over-express HB-EGF, or a cancer that is in contact with cells that over-express HB-EGF. The cancer can consist exclusively of cells that over-express HB-EGF or the cancer may include a sub-population of cells that over-express HB-EGF. The term "over-expression of HB-EGF" as used herein refers to cells that have increased levels of HB-EGF on the cell surface, or cells that excrete increased levels of HB-EGF, when compared to wild-type cells. The term "cells that over-express HB-EGF" also include cells that secrete or have on their cell surface HB-EGF with a gain of function mutation. Increased levels, as compared to wild-type, includes 1% or more, 5% or more, 10% or more, 20% or more, 50% or more, 100% or more, 5× or more, 10× or more, 100× or more, 1000× or more HB-EGF when compared wild-type.

A cancer that is "unresponsive to treatment by one or more Epidermal Growth Factor Receptor tyrosine kinase inhibitors" (EGFR-TKIs), is a cancer that does not respond to treatment with EGFR-TKIs. Thus, a subject having such a cancer will not be responsive to treatment with EGFR-TKIs. While the subject having such a cancer may initially respond to treatment, e.g., the cancer my initially go in remission or further growth of the cancer may initially be suppressed, the cancer will ultimately become resistant to treatment by the EGFR-TKIs and the cancer will no longer respond to treatment. EGFR-TKIs that are used in cancer therapy are known in the art and include Iressa (gefinitib) and Tarceva (erlontinib).

Therapeutically Effective Amount

In some embodiments, the compounds of the invention can be used in therapeutically effective amounts. The term "therapeutically effective amount" or "effective amount", which can be used interchangeably, refers to the amount necessary or sufficient to realize a desired therapeutic effect, e.g., shrinkage of a tumor, inhibition or suppression of cell proliferation, or increase of the percentage of apoptotic cells in a population of cells. Combined with the teachings provided herein, by choosing among the various active compounds and weighing factors such as potency, relative bioavailability, subject body weight, severity of adverse side-effects and preferred mode of administration, an effective prophylactic or therapeutic treatment regimen can be selected which does not cause substantial toxicity and yet is effective to treat the particular subject.

The effective amount for any particular application can vary depending on such factors as the disease or condition being treated, the particular myrsinoic acid A or myrsinoic acid A analogs being administered, the size of the subject, or the severity of the disease or condition. One of ordinary skill in the art can empirically determine the effective amount of a particular compound of the invention (i.e., myrsinoic acid A or myrsinoic acid A analog) and/or one or more other therapeutic agent without necessitating undue experimentation. It is preferred generally that a maximum dose be used, that is, the highest safe dose according to some medical judgment. Multiple doses per day may be contemplated to achieve appropriate systemic levels of compounds. Appropriate system levels can be determined by, for example, measurement of the patient's peak or sustained plasma level of the drug.

In some embodiments, a therapeutically effective amount is less than 50 mg/kg, such as less than 45 mg/kg, less than 40 mg/kg, less than 35 mg/kg, less than 30 mg/kg, less than 25 mg/kg, less than 20 mg/kg or less than 15 mg/kg. In some embodiments, a therapeutically effective amount is less than 10 mg/kg, such as less than 9 mg/kg, less than 8 mg/kg, less than 7 mg/kg, less than 6 mg/kg, less than 5 mg/kg, less than 4 mg/kg, less than 3 mg/kg or less than 2 mg/kg. In some embodiments, a therapeutically effective amount is less than 1.5 mg/kg, such as less than 1.4 mg/kg, less than 1.3 mg/kg, less than 1.2 mg/kg, less than 1.1 mg/kg, less than 1 mg/kg, less than 0.9 mg/kg, less than 0.8 mg/kg, less than 0.7 mg/kg, less than 0.6 mg/kg, less than 0.5 mg/kg, less than 0.4 mg/kg, less than 0.3 mg/kg, less than 0.2 mg/kg or less than 0.1 mg/kg.

In some embodiments, the therapeutically effective amount is administered in one dose. In some embodiments, the therapeutically effective amount is administered in multiple doses. Dosage may be adjusted appropriately to achieve desired compound levels, local or systemic, depending upon the mode of administration. For example, it is expected that intravenous administration would require a lower dose than oral delivery to result in the same therapeutically effective amount. In the event that the response in a subject is insufficient at such doses, even higher doses (or effective higher doses by a different, more localized delivery route) may be employed to the extent that subject tolerance permits. Multiple doses per day are contemplated to achieve appropriate systemic levels of compounds.

Pro-Drugs

The invention also embraces the administration of pro-drugs of myrsinoic acid A prodrugs of myrsinoic acid A analogs. The term "prodrug" as used herein refers to any compound that when administered to a biological system generates a biologically active compound (i.e., myrsinoic acid A or myrsinoic acid A analog) as a result of spontaneous chemical reaction(s), enzyme catalyzed chemical reaction(s), and/or metabolic chemical reaction(s), or a combination of two or more of these reactions. Standard prodrugs are formed using groups attached to functionality, e.g. HO—, HS—, HOOC—, $R_2N$—, associated with the drug, that cleave in vivo. Standard prodrugs include, but are not limited to, carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. The groups illustrated are exemplary, not exhaustive, and one skilled in the art could prepare other known varieties of prodrugs. Prodrugs can undergo some form of a chemical transformation to produce the compound that is biologically active or is a precursor of the biologically active compound. In some cases, the prodrug is biologically active, usually less than the drug itself, and serves to improve drug efficacy or safety through improved oral bioavailability, pharmacodynamic half-life, etc. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Prodrugs are described, for example, in The Organic Chemistry of Drug Design and Drug Action, by Richard B. Silverman, Academic Press, San Diego, 1992. Chapter 8: "Prodrugs and Drug Delivery Systems" pp. 352-401; Design of Prodrugs, edited by H. Bundgaard, Elsevier Science, Amsterdam, 1985; Design of Biopharmaceutical Properties through Prodrugs and Analogs, Ed. by E. B. Roche, American Pharmaceutical Association, Washington, 1977; and Drug Delivery Systems, ed. by R. L. Juliano, Oxford Univ. Press, Oxford, 1980.

Anti-Cancer Compounds

In some embodiments, myrsinoic acid A and/or one or more myrsinoic acid A analogs can be administered combined with other therapeutic agents (Also defined herein as a non-myrsinoic acid A anti-cancer compounds). The myrsinoic acid A and/or one or more myrsinoic acid A analogs and other therapeutic agent may be administered simultaneously or sequentially. When the other therapeutic agents are administered simultaneously they can be administered in the same or separate formulations, but are administered at the same time. The other therapeutic agents are administered sequentially with one another and with myrsinoic acid A and/or one or more myrsinoic acid A analogs, when the administration of the other therapeutic agents and the myrsinoic acid A and/or one or more myrsinoic acid A analogs is temporally separated. The separation in time between the administration of these compounds may be a matter of minutes or it may be longer.

In some embodiments, the other therapeutic agent is an anti-cancer compound. As used herein, an "anti-cancer compound" refers to an agent which is administered to a subject for the purpose of treating a cancer. Anti-cancer compounds include, but are not limited to anti-proliferative compounds, anti-neoplastic compounds, anti-cancer supplementary potentiating agents and radioactive agents. One of ordinary skill in the art is familiar with a variety of anti-cancer agents, or can find those agents in the routine art, which are used in the medical arts to treat cancer.

Anti-cancer compounds include, but are not limited to, the following sub-classes of compounds: Antineoplastic agents such as: Acivicin; Aclarubicin; Acodazole Hydrochloride; Acronine; Adozelesin; Adriamycin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Buniodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorombucil; Cirolemycin; Cisplatin; Cladribine; Crisnatol Mesylate; Cyclophosphamide; Cytarabine; Dacarbazine; DACA (N-[2-(Dimethyl-amino)ethyl]acridine-4-carboxamide); Dactinomycin; Daunorubicin Hydrochloride; Daunomycin; Decitabine; Dexormaplatin; Dezaguanine; Dezaguanine Ifesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131; Etoposide; Etoposide Phosphate; Etoprine; Fadrozole Hydrochloride; Fazarabine; Fenretinide; Floxuridine; Fludarabine Phosphate; Fluorouracil; 5-FdUMP; Flurocitabine; Fosquidone; Fostriecin Sodium; Gemcitabine; Gemcitabine Hydrochloride; Gold Au 198; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin, Mitosper; Mitotane; Mitoxantrone Hydrochloride; Mycophenolic Acid; Nocodazole; Nogalamycin; Ormaplatin; Oxisuran; Paclitaxel Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Thymitaq; Tiazofurin; Tirapazamine; Tomudex; TOP-53; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine; Vinblastine Sulfate; Vincristine; Vincristine Sulfate, Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride; 2-Chlorodeoxyadenosine; 2'-Deoxyformycin; 9-aminocamptothecin; raltitrexed; N-propargyl-5,8-dideazafolic acid, 2-chloro-2'-arabino-fluoro-2'-deoxyadenosine; 2-chloro-2'-deoxyadenosine; anisomycin; trichostatin A; hPRL-G129R; CEP-751; linomide; Piritrexim Isethionate; Sitogluside; Tamsulosin Hydrochloride and Pentomone.

Anti-neoplastic compounds include, but are not limited to 20-epi-1,25 dihydroxyvitamin D3; 5-ethynyluracil; abiraterone; aclarubicin; acylfulvene; adecypenol; adozelesin; aldesleukin; ALL-TK antogonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; antidorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III analogs; balanol; batimastat; BCR/ABL antagonists; benzochlorins; benzoylstaurosporine; beta lactam analogs; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin analogs (e.g., 10-hydroxy-camptothecin); canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin 13; combretastatin A4; combretastatin analogue; conagenin; crambescidin 816; crisnatol; cryptophycin 8; cryptophycin A analogs; curacin A; cyclopentanthraquinones; cycloplatam; cypemycin; cytarabine ocfosfate; cytolytic factor; cytostatin; dacliximab; decitabine; dehydrodidemnin 10 deslorelin;

dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; discodermolide; docosanol; dolasetron; doxifluridine; droloxifene; dronabinol; duocarmycin SA; ebselen; ecomustine; edelfosine; edrecolomab; eflornithine; elemene; emitefur; epirubicin; epothilones (A, R=H; B, R=Me); epithilones; epristeride; estramustine analogue; estrogen agonists; estrogen antagonists; etanidazole; etoposide; etoposide 4'-phosphate (etopofos); exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mithracin; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor, multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; oracin; oral cytokine inducer; ormaplatin; osaterone; oxaliplatin; oxaunomycin; paclitaxel analogues; paclitaxel analogs; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; podophyllotoxin; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; Sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

Anti-cancer supplementary potentiating agents include, but are not limited to, Tricyclic anti-depressant drugs (e.g., imipramine, desipramine, amitryptyline, clomipramine, trimipramine, doxepin, nortriptyline, protriptyline, amoxapine and maprotiline); non-tricyclic anti-depressant drugs (e.g., sertraline, trazodone and citalopram); $Ca^{2+}$ antagonists (e.g., verapamil, nifedipine, nitrendipine and caroverine); Calmodulin inhibitor (e.g. prenylamine, trifluoroperazine and clomipramine); Amphotericin B; Triparanol analogues (e.g. tamoxifen); antiarrhythmic drugs (e.g., quinidine); antihypertensive drugs (e.g. reserpine); Thiol depleters (e.g., buthionine and sulfoximine) and Multiple Drug Resistance reducing agents such as Cremaphor EL. The compounds of the invention also can be administered with cytokines such as granulocyte colony stimulating factor.

Radioactive agents include but are not limited to Fibrinogen I 125; Fludeoxyglucose F18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate-Hg 203; Merisoprol Hg 197; Selenomethionine Se 75; Technetium Tc 99 m Atimony Trisulfide Colloid; Technetium Tc 99 m Bicisate; Technetium Tc 99 m Disofenin; Technetium Tc 99 m Etidronate; Technetium Tc 99 m Exametazime; Technetium Tc 99 m Furifosmin; Technetium Tc 99 m Gluceptate; Technetium 99 m Lidofenin; Technetium Tc 99 mm Mebrofenin; Technetium Tc 99 m Medronate; Technetium Tc 99 m Medronate Disodium; Technetium Tc 99 m Mertiatide; Technetium Tc 99 m Oxidronate; Technetium Tc 99 m Pentetate; Technetium Ic 99 m Pentetate Calcium Trisodium; Technetium Tc 99 m Sestamibi; Technetium Tc 99 m Siboroxime; Technetium Tc 99 m Succimer; Technetium Tc 99 m Sulfur Colloid; Technetium Tc 99 m Teboroxime; Technetium Tc 99 m Tetrofosmin; Technetium Tc 99 m Tiatide; Thyroxine I 125: Thyroxine I 131; Tolpovidone I 131; Triolein I 125; Triolein I 131.

In some embodiments, the compounds of the invention are administered in conjunction with an anti-cancer therapy. Anti-cancer therapies include, but are not limited to, the administration of anti-cancer compounds, radiation and surgical procedures.

Pharmaceutical Compositions and Routes of Administration

The compounds of the invention typically are administered as pharmaceutical compositions, which may routinely contain pharmaceutically acceptable concentrations of salt, buffering agents, preservatives, compatible carriers, adjuvants, and optionally other therapeutic ingredients. The nature of the pharmaceutical carrier and other components of the pharmaceutical composition will depend on the mode of administration.

The pharmaceuticals compositions of the invention may be administered by any means and route known to the skilled artisan in carrying out the treatment methods described herein. Preferred routes of administration include but are not limited to oral, parenteral, intratumoral, intramuscular, intranasal, intracranial, sublingual, intratracheal, inhalation, ocular, vaginal, and rectal.

For oral administration, the compounds of the invention can be formulated readily by combining the compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, e.g., EDTA for neutralizing internal acid conditions, or may be administered without any carriers.

For the compounds of the invention, the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection the compound or by release of the biologically active compound beyond the stomach environment, such as in the intestine. To ensure full gastric resistance a coating impermeable to at least pH 5.0 is desired. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films. A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic powder; for liquid forms, a soft gelatin shell may be used. The shell material of cachets could be thick starch or other edible paper. For pills, lozenges, molded tablets or tablet triturates, moist massing techniques can be used.

The compounds of the invention can be included in the formulation as fine multi-particulates in the form of granules or pellets of particle size about 1 mm. The formulation of the material for capsule administration could also be as a powder, lightly compressed plugs or even as tablets. The pharmaceutical composition could be prepared by compression. Colorants and flavoring agents may all be included. For example, the compounds of the invention may be formulated (such as by liposome or microsphere encapsulation) and then further contained within an edible product, such as a refrigerated beverage containing colorants and flavoring agents. One may dilute or increase the volume of the pharmaceutical composition with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the pharmaceutical composition into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants. Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic. An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000. Glidants that might improve the flow properties of the drug during formulation and to aid rearrangement during compression might be added. The glidants may include starch, talc, pyrogenic silica and hydrated silicoaluminate.

To aid dissolution of the compounds of the invention into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the compounds of the invention or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds of the invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the compounds of the invention. The compounds of the invention may delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass. All such devices require the use of formulations suitable for the dispensing the compounds of the invention. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified compounds of the invention may also be prepared in different formulations depending on the type of chemical modification or the type of device employed. Formulations suitable for use with a nebulizer, either jet or ultrasonic, will typically comprise the compounds of the invention dissolved in water at a concentration of about 0.1 to 25 mg of biologically active compound. The formulation may also include a buffer and a simple sugar. The nebulizer formulation may also contain a surfactant, to reduce or prevent surface induced aggregation caused by atomization of the solution in forming the aerosol.

Formulations for use with a metered-dose inhaler device will generally comprise a finely divided powder containing the compounds of the invention suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant. Formulations for dispensing from a powder inhaler device will comprise a finely divided dry powder containing the compounds of the invention and may also include a bulking agent, such as lactose, sorbitol, sucrose, or mannitol in amounts which facilitate dispersal of the powder from the device, e.g., 50 to 90% by weight of the formulation. The compounds of the invention should most advantageously be prepared in particulate form with an average particle size of less than 10 mm (or microns), most preferably 0.5 to 5 mm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran. For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available. Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds of the invention, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

The compounds may also be formulated in rectal or vaginal compositions such as suppositories or retention enemas, e.g., containing conventional suppository bases such as cocoa butter or other glycerides. In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble analogs, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose analogs, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or one or more auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, 1990, Science 249, 1527-1533, which is incorporated herein by reference.

The compounds of the invention and optionally other therapeutics, including non-myrsinoic acid A anti-cancer compounds, may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of one or more compounds of the invention and optionally additional therapeutic agents included in a pharmaceutically-acceptable carrier. The term pharmaceutically-acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The compounds of the invention may be provided in particles. Particles as used herein means nano or microparticles (or in some instances larger) which can consist in whole or in part of the compounds of the invention or the other therapeutic agent(s) as described herein. The particles may contain the compounds of the invention in a core surrounded by a coating, including, but not limited to, an enteric coating. The compounds of the invention also may be dispersed throughout the particles. The compounds of the invention also may be adsorbed into the particles. The particles may be of any order release kinetics, including zero order release, first order release, second order release, delayed release, sustained release, immediate release, and any combination thereof, etc. The particle may include, in addition to the compounds of the invention, any of those materials routinely used in the art of pharmacy and medicine, including, but not limited to, erodible, nonerodible, biodegradable, or nonbiodegradable material or combinations thereof. The particles may be microcapsules which contain the compounds of the invention in a solution or in a semi-solid state. The particles may be of virtually any shape.

Both non-biodegradable and biodegradable polymeric materials can be used in the manufacture of particles for delivering the compounds of the invention. Such polymers may be natural or synthetic polymers. The polymer is selected based on the period of time over which release is desired. Bioadhesive polymers of particular interest include bioerodible hydrogels described by Sawhney et. al., 1993, Macromolecules 26, 581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The compounds of the invention may be contained in controlled release systems. The term "controlled release" is intended to refer to any compound of the invention-containing formulation in which the manner and profile of compound release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a compound over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the compound there from. "Delayed release" may or may not involve gradual release of a compound over an extended period of time, and thus may or may not be "sustained release." Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

Kits

In one aspect the invention provides kits comprising a pharmaceutical composition comprising a therapeutically effective amount of myrsinoic acid A and/or one or more myrsinoic acid A analogs and instructions for administration of the pharmaceutical composition. In some aspects of the invention, the kit can include a pharmaceutical preparation vial, a pharmaceutical preparation diluent vial, and the compound of the invention. The diluent vial contains a diluent such as physiological saline for diluting what could be a concentrated solution or lyophilized powder of the compound of the invention. In some embodiments, the instructions include instructions for mixing a particular amount of the diluent with a particular amount of the concentrated pharmaceutical preparation, whereby a final formulation for injection or infusion is prepared. In some embodiments, the instructions include instructions for use in a syringe or other administration device. In some embodiments, the instructions include instructions for treating a patient with an effective amount of the compounds of the invention. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove.

EXAMPLES

Example 1

Screening of Compounds for Binding to HB-EGF

Experimental Small Molecule Microarray slides (Prepared by Angela Khoeler, Broad Institute, Cambridge, Mass.) were incubated on parafilm (Alcon, Menasha Wis.) with 300 µL of a 25 µg/mL rGST-HB-EGF (glutathione S-transferase-HB EGF) solution in a PBS (phosphate buffered saline) solution with 0.1% BSA (bovine serum albumin). Control slides were incubated with 300 µL of PBS buffer with 0.1% BSA. All slides were allowed to incubate for one hour at room temperature followed by washing each slide with PBS buffer three times. Each slide was subsequently incubated with 300 µL of a 5 µg/mL anti-GST antibody solution (Promega Inc.) in TBS (tris-buffered saline) with 0.1% BSA. After one hour of incubation, the slides were washed with TBS buffer three times. Each slide was then incubated at room temperature for one hour with the secondary fluorescent labeled antibody in TBST (tris-buffered saline with tween) with 0.1% BSA followed by three washes with PBST (phosphate buffered saline with tween). Slides were dried by centrifugation and scanned with a GenePix 4000B microarray plate reader (Axon Instruments, Sunnyvale, Calif.). Data analysis was performed with GenePix Pro software (Axon Instruments). The Experimental setup is shown in FIG. 1.

Example 2

Surface Plasmon Resonance Shows Binding of Myrsinoic Acid A to HB-EGF

A Biacore™ T100 (GE Healthcare, Uppsala, Sweden) was used to perform the Surface Plasmon Resonance (SPR) experiments. Sensor surface preparation and interaction analyses experiments were performed at 25° C. Prior to surface preparation, lyophilized HB-EGF protein (R&D Systems) was dissolved in either water or PBS buffer, at pH 7.4 and protein purity determined by Nu-Page 4-12% Bis-Tris gel in MOPS (3-(N-Morpholino)-propanesulfonic acid) buffer with a silver stain sensor preparation. HB-EGF was immobilized onto series S sensor chip CM4 via a standard N-ethyl-N'-(dimethyl-aminopropyl)carbodiimide/N-hydroxysuccinimide (EDC/NHS) amine coupling procedures. HB-EGF was diluted to 10 µg/mL in 10 mM sodium acetate pH5.5 for these procedures and resultant immobilization levels were 1000-1200 R.U.s. (R.U.: Relative Units). Control surfaces were prepared similarly without protein derivatization and utilized as a reference surfaces for compound binding experiments. For compound interaction analyses, 0.01 M Hepes, pH7.4, 0.15 M NaCl, 0.05% Surfactant P20 and 5% DMSO was used. Compound samples were prepared by serial dilution in the range 0.78 uM-50 uM and flowed over control and derivatized surfaces for two minutes at a flow-rate of 80 µL/min. Zero concentration blank buffer cycles were included as negative control samples. Solvent correction procedures were included to compensate for any DMSO related bulk refractive index variations and performed as described previously. Non-specific binding effects to sensor surface CM4 (a type of sensor, used for a positive control binding) were absent for all analyses reported.

Data analysis was carried out using Biacore T100 evaluation software v1.1.1. Data were prepared by subtraction of reference surface data and blank buffer sample data, a procedure commonly referred to as 'double referencing'. Solvent correction was applied.

Figure 2:
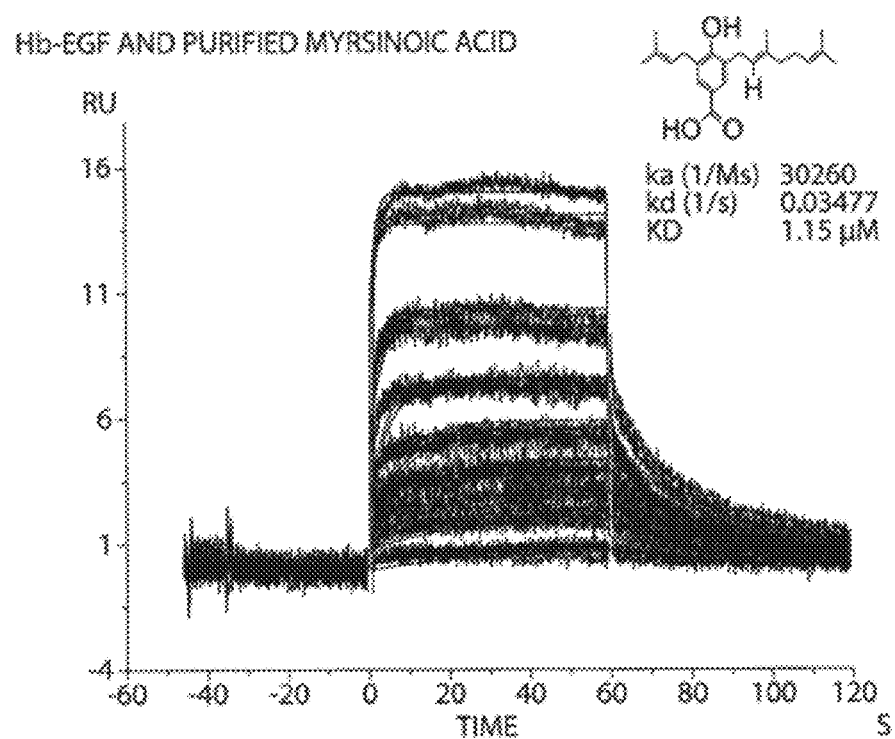
FIG. 2 shows the binding of myrsinoic acid A to HB-EGF by Surface Plasmon Resonance.
Figure 4:
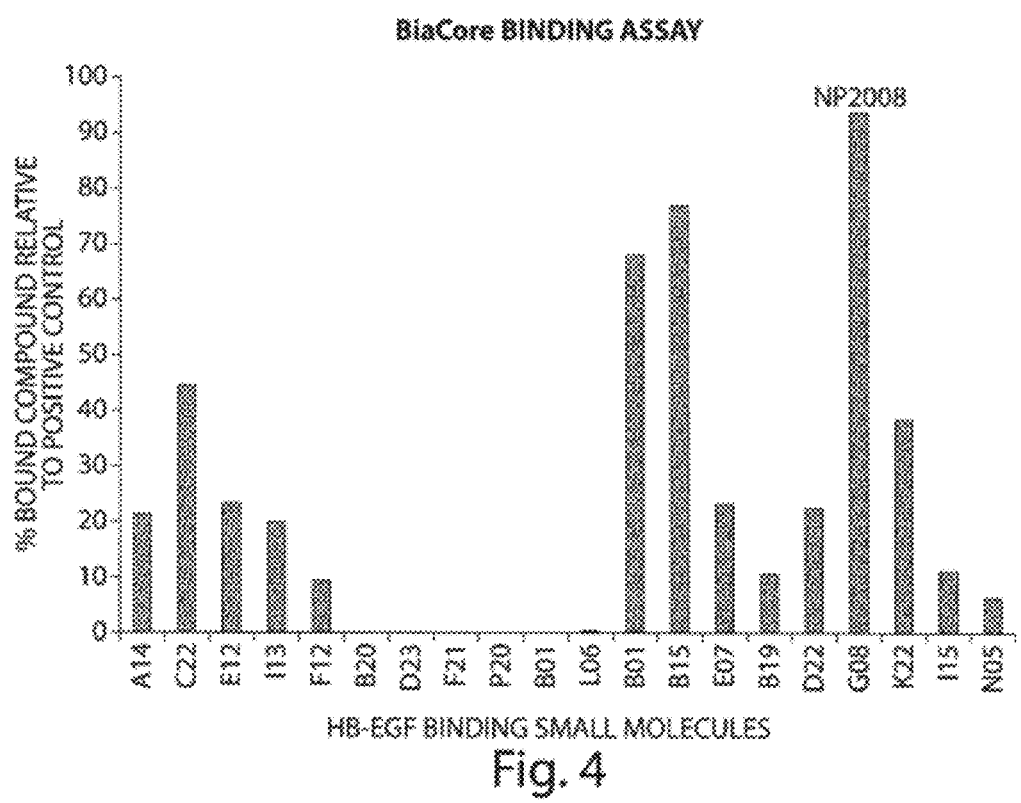
FIG. 4 shows the result of a screen for the binding of small molecules to HB-EGF in a BiaCore assay. The binding of myrsinoic acid A (NP2008) is identified.

FIG. 2 shows the binding of myrsinoic acid A to HB-EGF, while FIG. 4 shows the binding of a number of compounds to HB-EGF. The binding of myrsinoic acid A (NP2008) is indicated.

Example 3

Figure 5A:
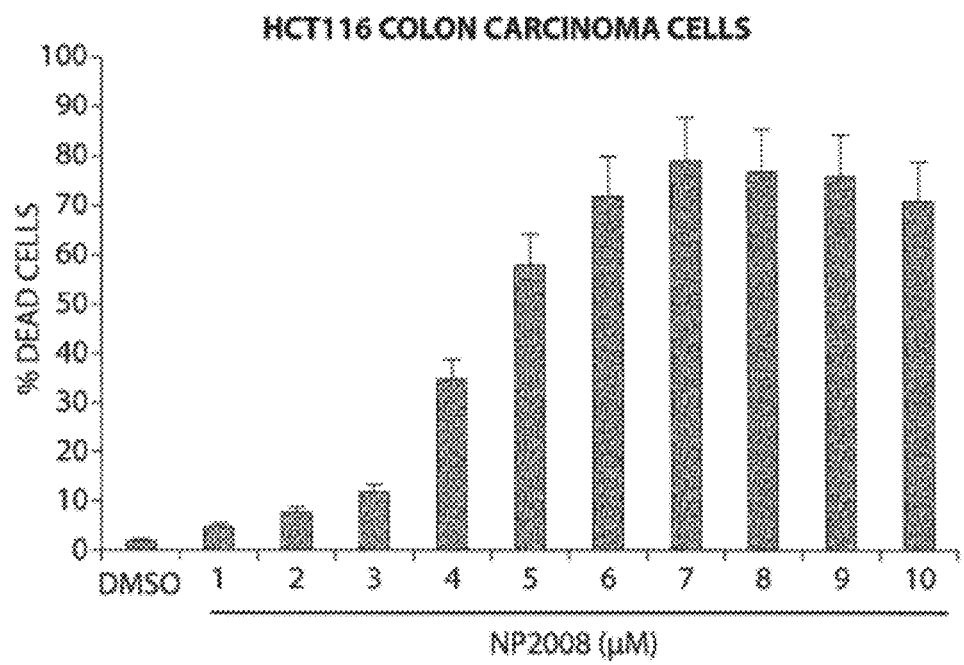
FIG. 5 shows the ability of myrsinoic acid A (NP2008) to induce cell death in the cancer cell lines HCT116 (colon carcinoma) (A) and MDA436 (breast carcinoma) (B).
Figure 5B:
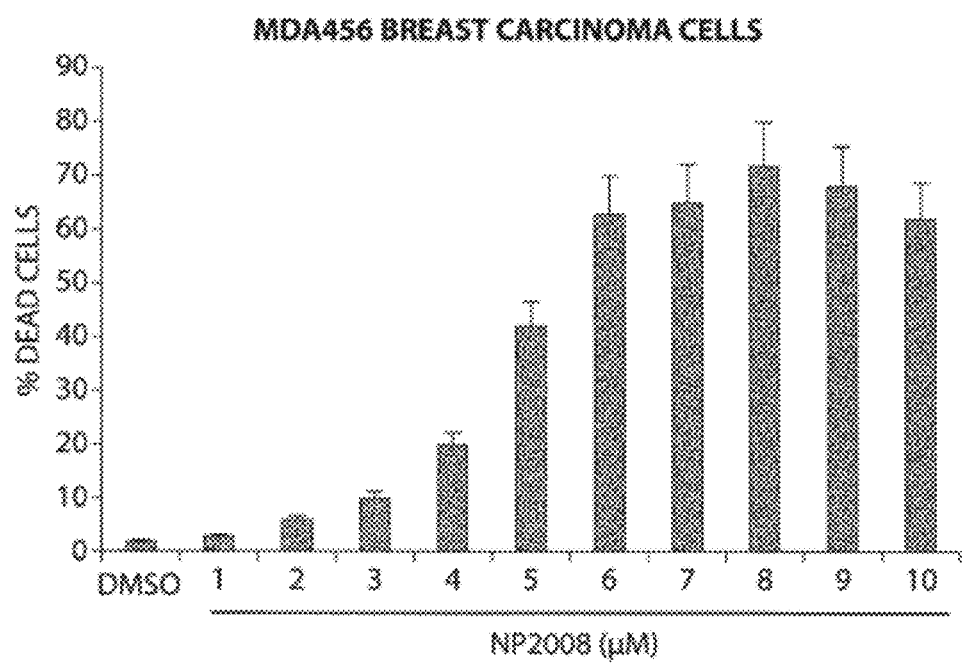

Myrsinoic Acid A Suppresses Cell Growth and Induces Apoptosis in a Variety of Cancer Cell Lines We evaluated the ability of myrsinoic acid A (NP2008) to suppress cell growth and induce apoptosis in a panel of human cancer cells. We found that myrsinoic acid A induced cell death/apoptosis in various human cancer cells including breast cancer cells, bladder cancer cells, colon cancer cells, and lung cancer cells. The ability to induce apoptosis was seen at micromolar potencies (2.5-10 microM) and was concentration dependent. The same result was observed for both cancer cell lines with wildtype p53 or with cancer cells with a mutated (inactive) version of p53. FIG. 5 shows that myrsinoic acid A (NP2008) induces cell death in EJ human bladder cancer cells (A) and in HCT116 human colon cancer cells (B).

Figure 6:
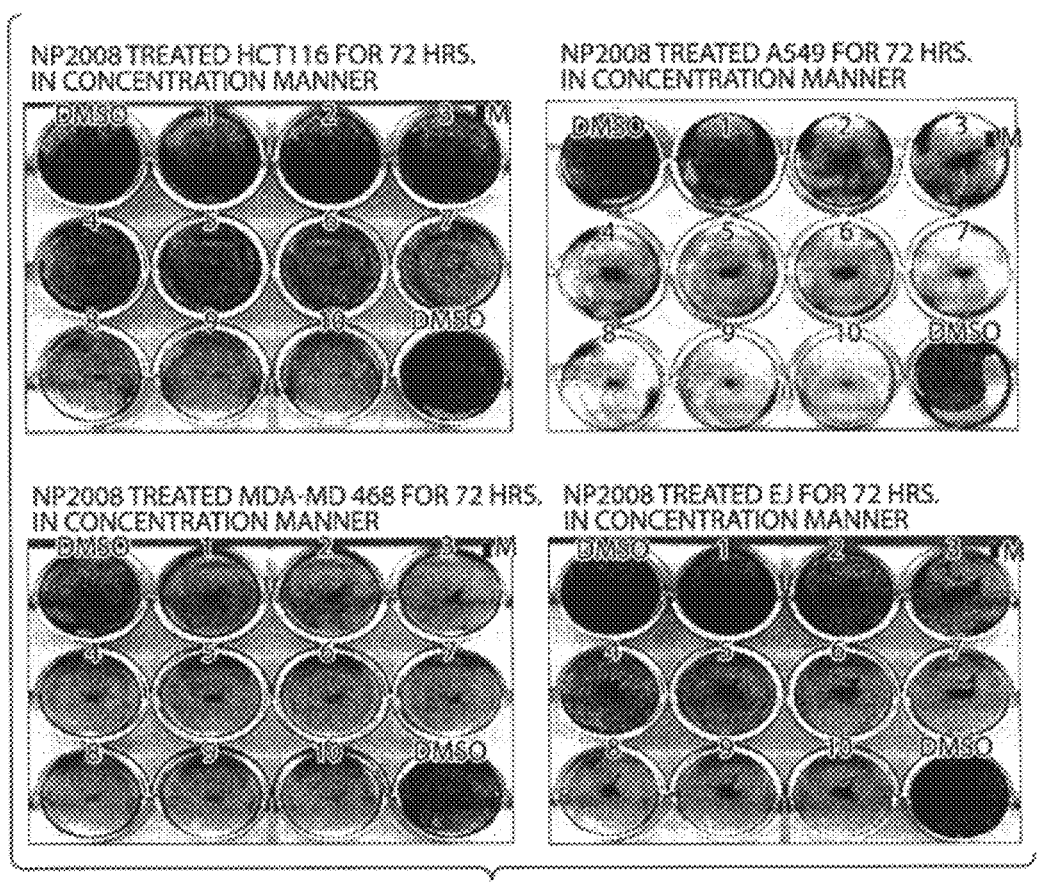
FIG. 6 shows the effect of myrsinoic acid A (NP2008) on cell viability for a number of cancer cell lines.

We also found that myrsinoic acid A inhibited tumor cell growth in various human cancer cells including breast cancer cells, bladder cancer cells, colon cancer cells, and lung cancer cells. The ability to suppress the growth of cancer cells was again seen at micromolar potencies (2.5-10 microM) and was concentration dependent. The same result was observed for both cancer cell lines with wildtype p53 or with cancer cells with a mutated (inactive) version of p53. FIG. 6 shows a decrease in the number viable cells after myrsinoic acid A (NP2008) treatment in EJ, HCT116, MDA-MD486 human breast cancer cells and A549 human carcinoma cells. Viable cells are shown with crystal-violet cell staining.

Example 4

Figure 7:
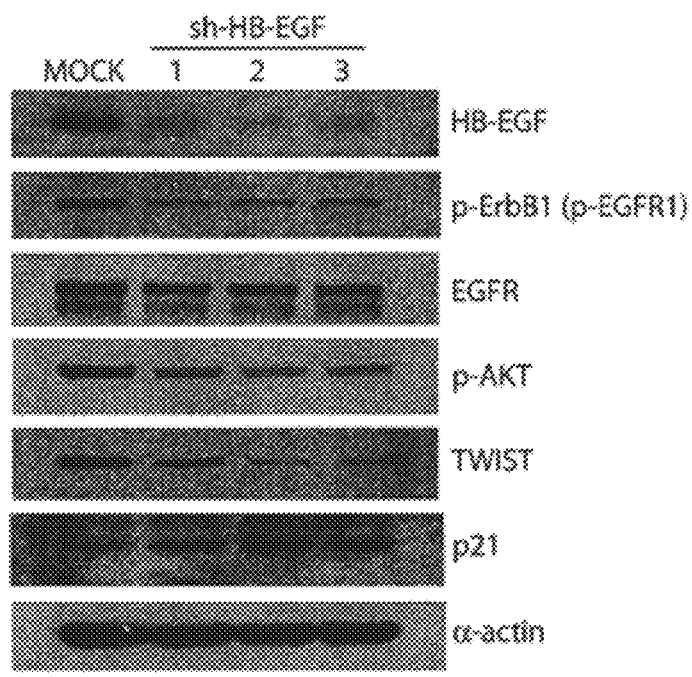
FIG. 7 shows that knocking down the expression of HB-EGF (by the introduction of sh-HB-EGF) results in the suppression of the EGFR signaling pathway.

Comparison of the Effects of HB-EGF Knockdown and Treatment with Myrsinoic Acid A (NP2008) on EGFR Signaling in Cancer Cells To evaluate the level of EGFR signaling in HB-EGF knockout cells, control EJ cells and EJ cells into which HB-EGF shRNA was introduced were lysed to determine the level of HB-EGF, phospho-ErbB1, EGFR, phospho-AKT, Twist and p21 expression by Western blot analysis. FIG. 7 shows that HB-EGF knock-down suppresses the expression of HB-EGF, phospho-ErbB1, phospho-AKT and Twist. Actin was used as a loading control in all experiments. (Lanes 1, 2 and 3 represent multiple samples)

Figure 8:
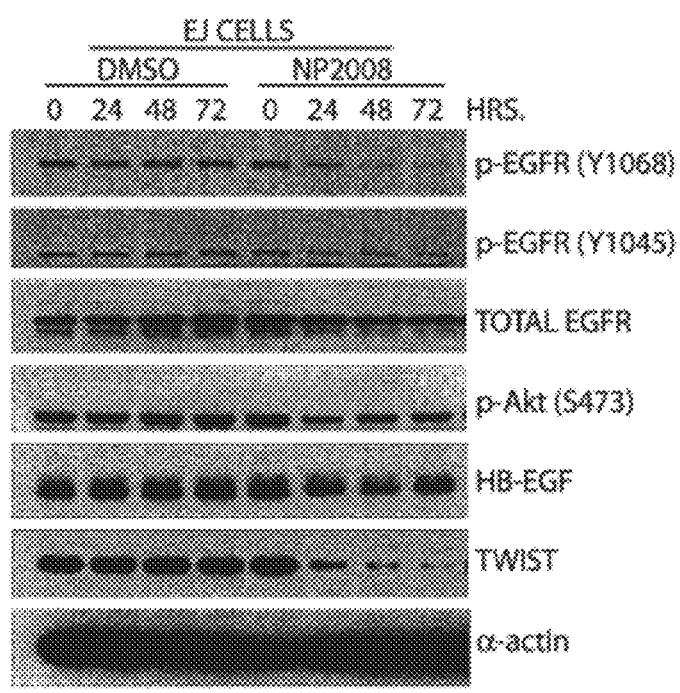
FIG. 8 shows that myrsinoic acid A (NP2008) suppresses the EGFR signaling pathway.

To evaluate the ability of myrsinoic acid A to suppress EGFR signaling, EJ cells were exposed to 10 microM myrsinoic acid A (NP2008) or DMSO as a control. The cells were lysed at different time points to determine the level of HB-EGF, phospho-ErbB1, EGFR, phospho-AKT, Twist and p21 expression by Western blot analysis (FIG. 8). A comparison between FIGS. 7 and 8 shows that a similar suppression in EGFR signaling was obtained after wild type EJ cells were exposed to myrsinoic acid A or when HB-EGF was knocked-out.

Example 5

Figure 9:
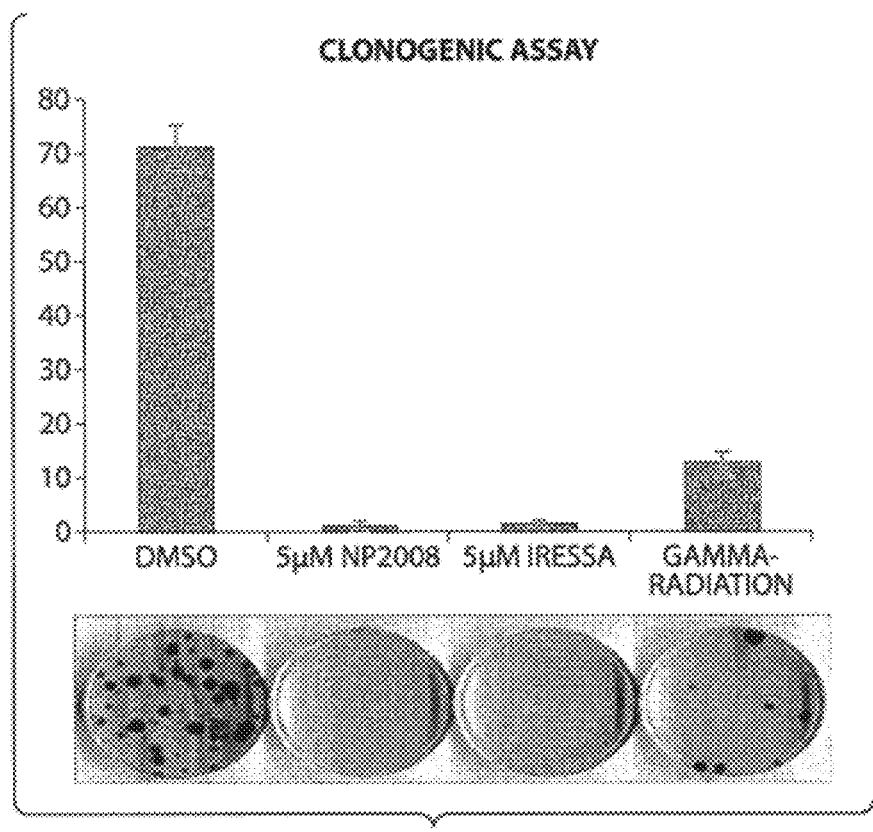
FIG. 9 shows that myrsinoic acid A (NP2008) is more effective in the suppression of the growth of EJ (bladder carcinoma) cancer cells than radiation or Iressa (gefinitib), as shown by a clonogenic assay.
Figure 10A:
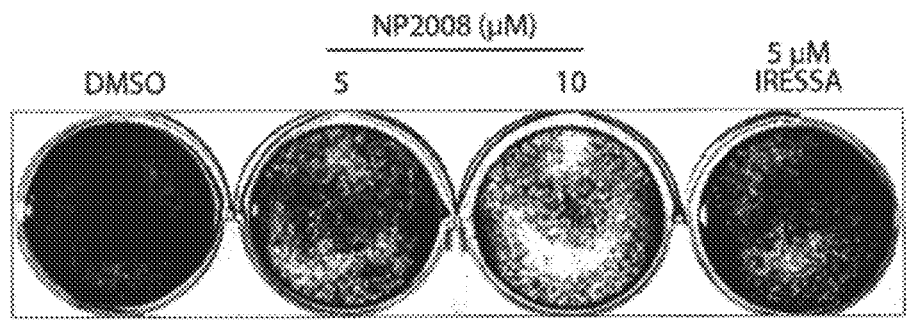
FIG. 10 shows that myrsinoic acid A (NP2008) is a more potent suppressor of cancer cell proliferation than Iressa (gefinitib), as shown by a cytotoxicity assay. FIGS. A and C show the results of experiments with high confluent density cells, while FIGS. B and D show the results of experiments with low confluent density cells.
Figure 10B:
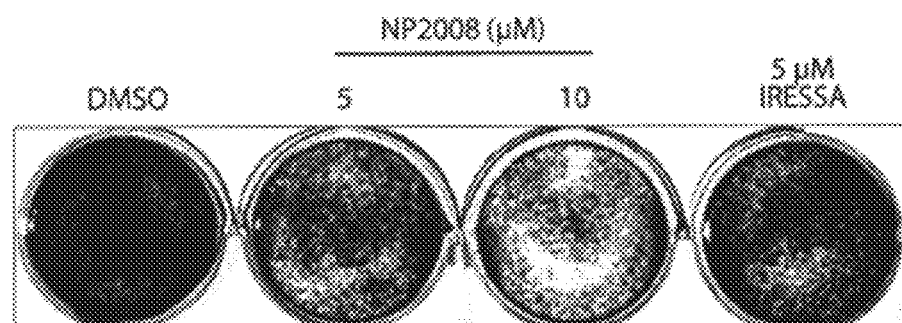
Figure 10C:
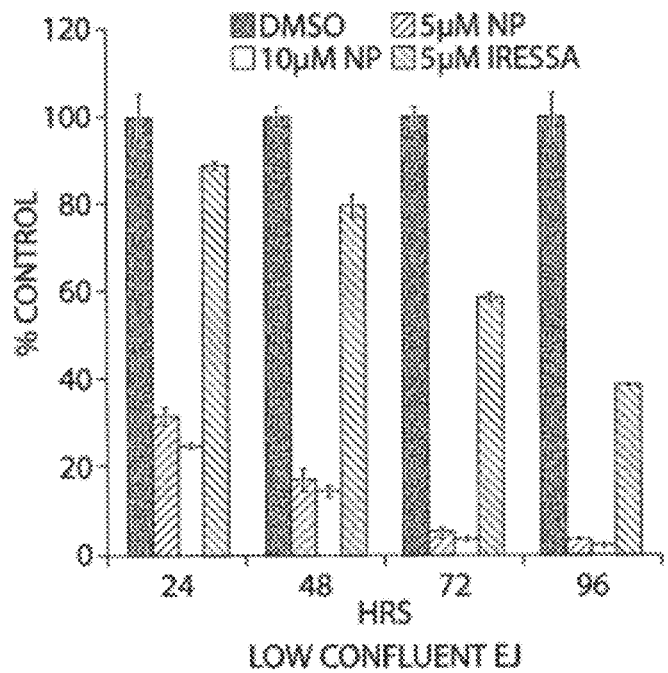
Figure 10D:
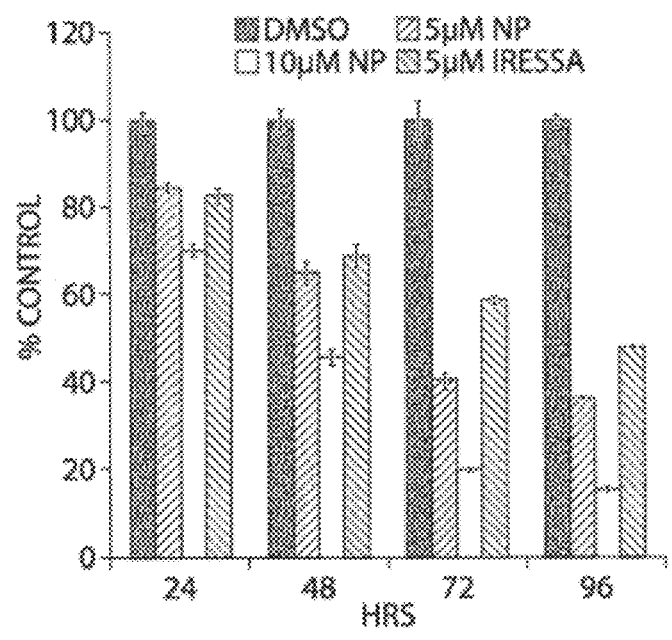
Figure 11:
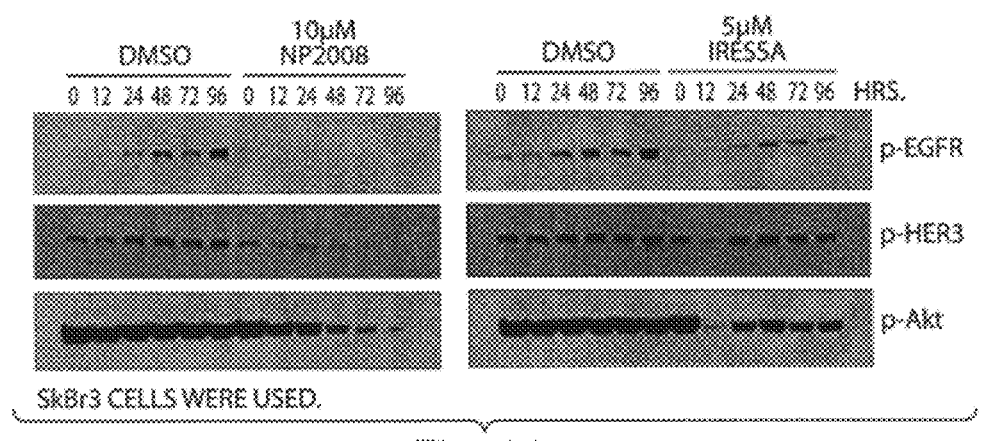
FIG. 11 shows that myrsinoic acid A (NP2008) can suppress EGFR signaling in an SkBr3 (breast) cancer cell line that is resistant to Iressa (gefinitib).

Comparison Between Myrsinoic Acid A, Iressa and Gamma-Radiation in the Ability to Suppress Cancer Cell Growth The ability to suppress cancer cell growth by myrsinoic acid A (NP2008), Iressa and gamma-radiation was evaluated with a clonogenic assay of EJ cells. Aliquots of one hundred EJ cells were plated out in petridish (60 mm size) and allowed to establish themselves. After 24 hours the cells were treated with myrsinoic acid A (NP2008; 5 µM), Iressa (5 µM), DMSO as a solvent control, or exposed to gamma-irradiation (10 Gy). After exposure, the cells were grown for two weeks without changing the medium, and the number of cell colonies were counted. The results are shown in FIG. 9. Both myrsinoic acid A and Iressa treated EJ cells did not show any colony growth.

Example 6

Comparison in Cancer Cell Cytotoxicity Between Myrsinoic Acid A and Iressa

EJ cancer cells were cultured to high or low confluent cell density and treated with two different concentrations of myrsinoic acid A (NP2008; 5 and 10 microM) or Iressa (5 microM). DMSO treatment was used as a control. Cells were stained with 0.4% sulforhodamine B three days after treatment. The results are shown in FIG. 10 A (cells started with higher confluent density) and FIG. 10 B (treatment experiments performed with lower confluent density). FIG. 10 C (low confluent) and FIG. 10 D show the result of a time curve experiment wherein aliquots of cells were stained at 24, 48, 72 and 96 hours.

Example 7

The Treatment of Iressa Resistant Cancer Cells with Myrsinoic Acid A

SKBR3 human breast cancer cells were treated with myrsinoic acid A (NP2008) or Iressa for 12, 24, 48, 72 or 96 hours. After treatment, total cell lysates were isolated and analyzed by Western blot analysis. The cells were evaluated for the presence of phospho-EGFR, phospho-Her3/ErbB3 and phospho-AKT. Iressa treatment initially suppressed phospho-EGFR, phospho-HER3 and phospho-AKT activation (12 and 24 hour time points). However, longer exposure to Iressa resulted in the activation of the EGFR signaling pathway as evidenced by the presence of phospho-EGFR, phopho-HER3 and phospho-AKT. In contrast, treatment with myrsinoic acid A resulted in the long term suppression of these proteins.

Example 8

Figure 12:
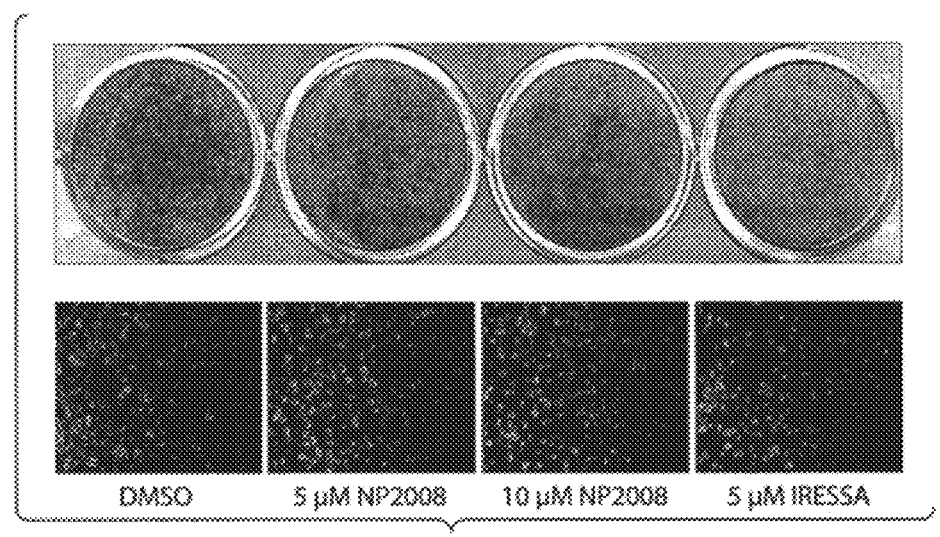
FIG. 12 shows that myrsinoic acid A (NP2008) is non-toxic to human normal (non-cancerous) breast epithelial cells.
Figure 13:
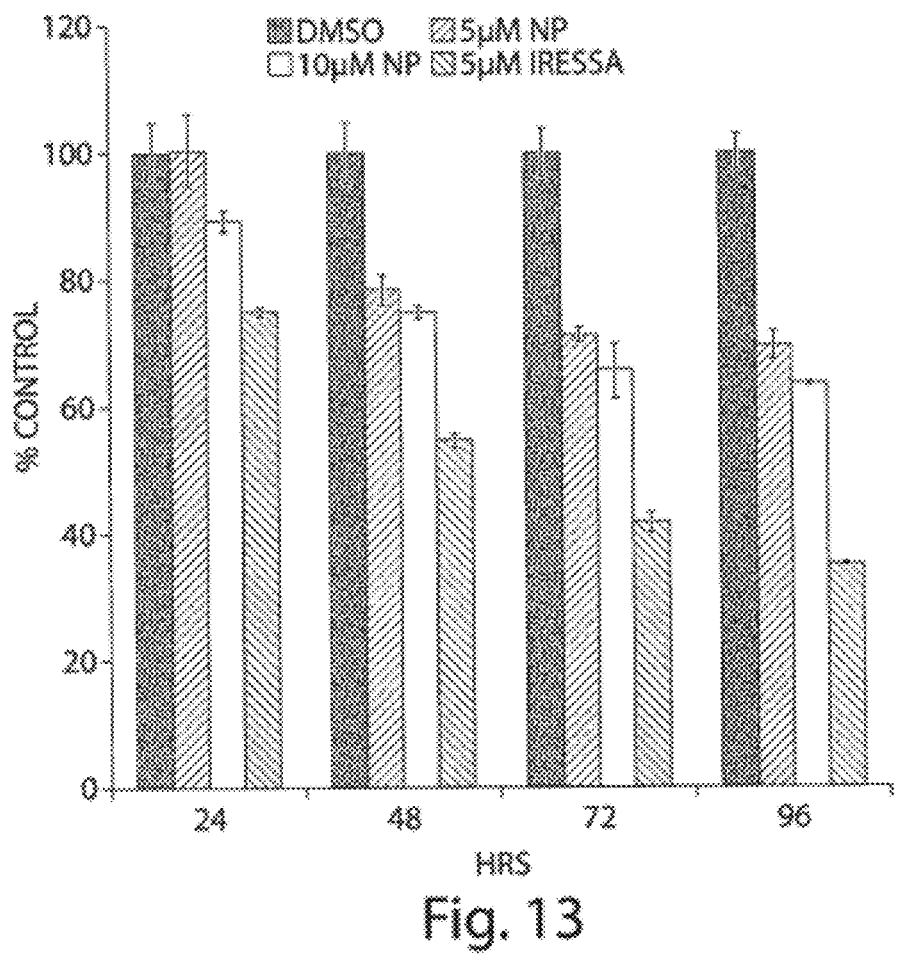
FIG. 13 provides a bar graph with data that show that myrsinoic acid A (NP2008) is non-toxic to human normal (non-cancerous) breast epithelial cells.

Treatment with Myrsinoic Acid A Shows Little Toxicity in Human Primary Normal (Non-Cancerous) Cells Normal cells were cultured and treated with myrsinoic acid A (NP2008) at 5 microM or 10 microM concentration or with Iressa (5 microM). The cultures were subsequently stained with crystal-violet blue to evaluate the number of live cells. Representative images are shown in FIG. 12. The results of a time-curve experiment are shown in FIG. 13. Normal cells were grown in 24 well plates and treated with myrsinoic acid (NP2008) (at 5 µM and 10 µM) or Iressa (5 microM) for the indicated times (24-96 hours). The number of dead cells was determined by Alamar Blue staining as well as Cyto-Flow-cell death assays from Promega (Madison, Wis.). The results depicted in FIG. 13 show that myrsinoic acid A shows less cytotoxicity in normal cells than Iressa.

Example 9

Myrsinoic Acid A is Effective in Suppressing Tumor Growth In Vivo

Figure 14:
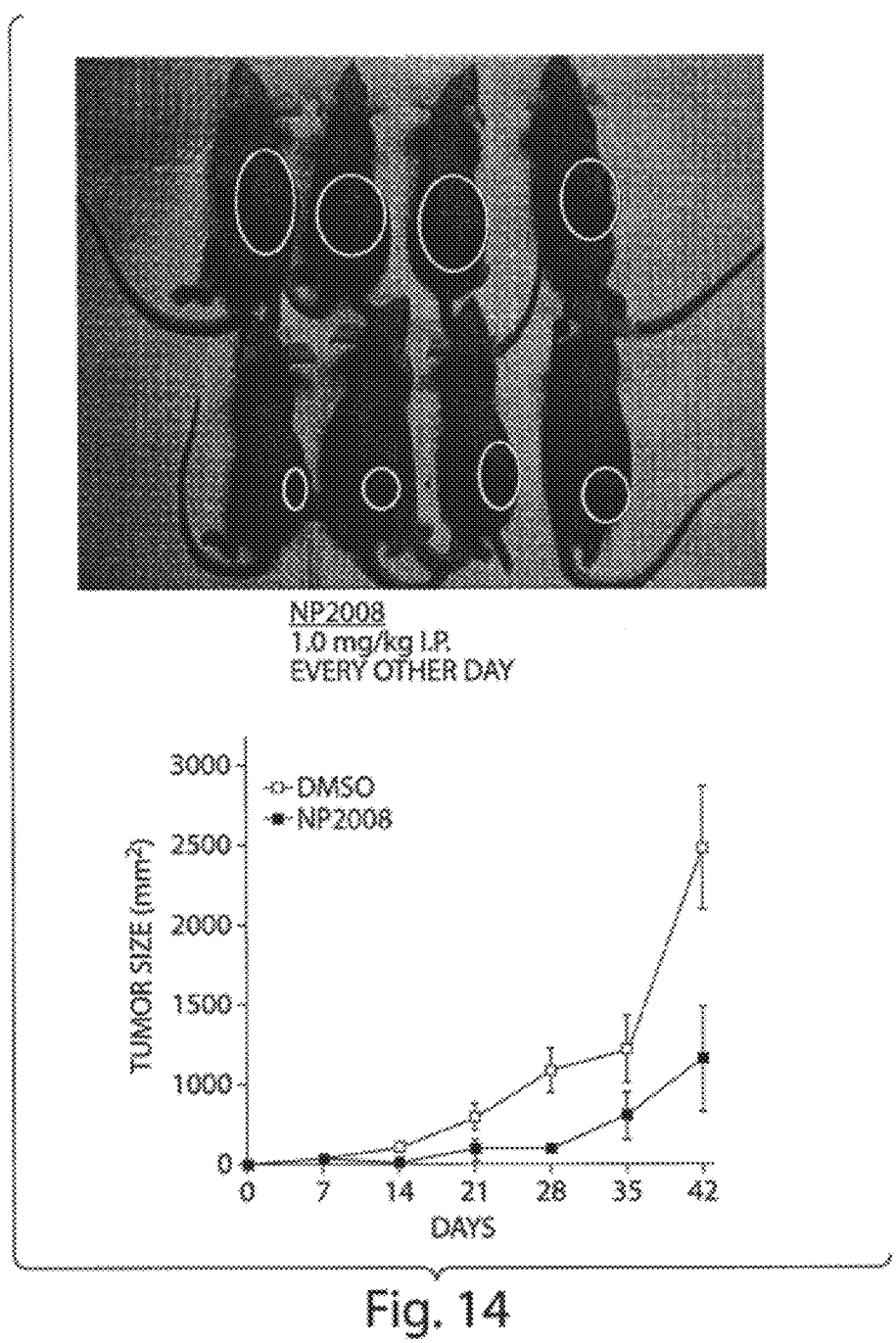
FIG. 14 shows that myrsinoic acid A (NP2008) can suppress tumor growth in a bladder cancer xenograft mouse model.

Lung or bladder tumor xenograft-bearing mice were treated with myrsinoic acid A to evaluate its in vivo antitumor effect. A total of $2\times10^6$ EJ cells or A549 cells were implanted subcutaneously on opposite site flanks in each nude/nude mice (Charles River, Mass.). There were six mice in each group. When tumor masses grew to ~2-5 mm in diameter, myrsinoic acid A (NP2008) was administered intraperitoneally (total 1 mg/kg) every 48 hours for 42 days. As shown in FIG. 14, significant tumor-growth suppression was observed in mice that were treated with myrsinoic acid A, as compared to control DMSO-administered mice.

Example 10

Myrsinoic Acid A Suppresses Tumor Progression in a Spontaneous Tumor Model

Mice with a spontaneous tumor model (MMTV-PvVT (FVB/N-Tg) transgenic mice; NCI repository) develop multifocal mammary tumor (from hyperplasia to metastatic) with a high incidence of metastasis. This mouse model has been widely used for the correlation studies of human cancer (Guy et al., Moll. Cell. Biol. 12: 954-961, 1992). In addition, this mouse model has been used to evaluate the effectiveness of potential drug therapies. Generally, due to aggressiveness of tumor growth and spread in this mouse-model, only a combination of chemo-drugs is effective in tumor growth inhibition in this mouse model.

Figure 15:
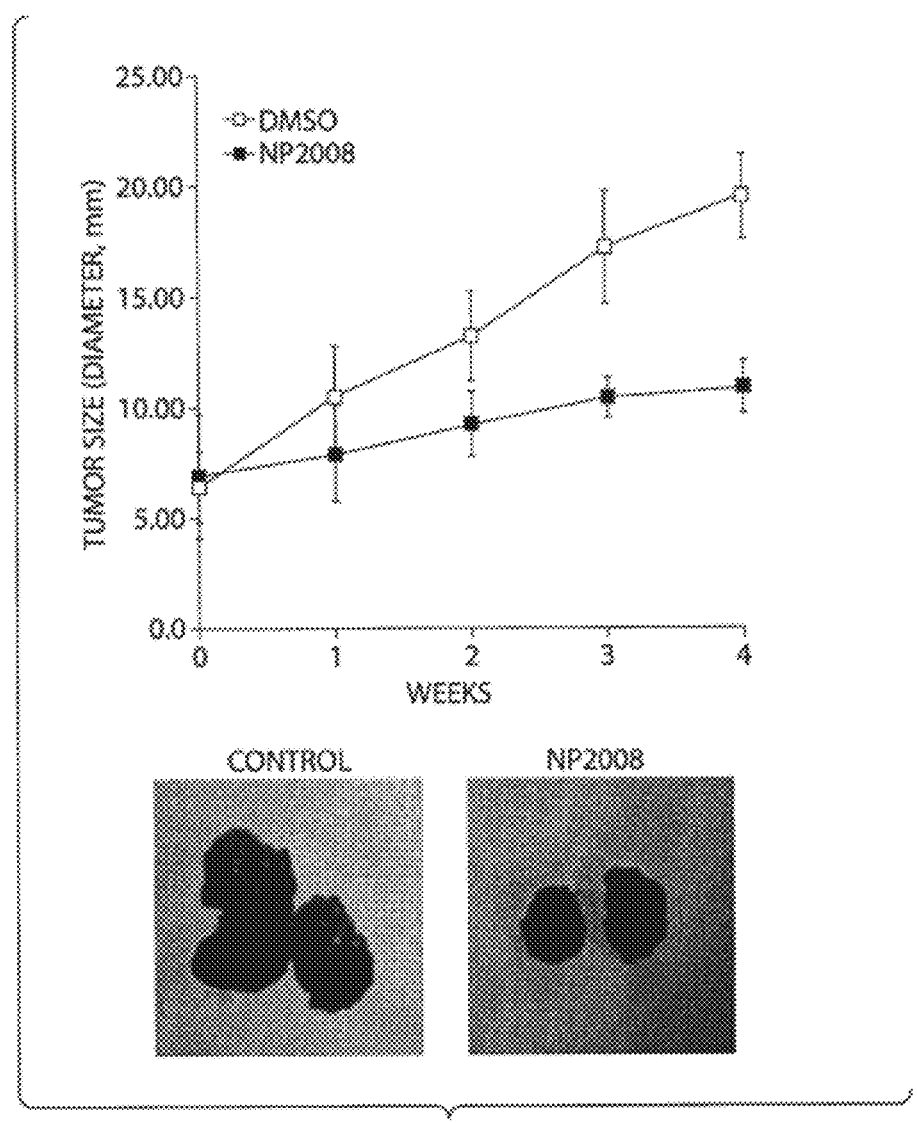
FIG. 15 shows that myrsinoic acid A (NP2008) can reduce the tumor mass as shown in a spontaneous tumor mouse model.

MMTV-PyVT mice were maintained until mammary tumor size reached to 6 mm, and then treated with myrsinoic acid A (NP2008) (5 mg/kg) or vehicle (DMSO) daily by i.p. for 28 days. FIG. 15 shows that a significant reduction in tumor mass was shown in myrsinoic acid A treated mice compared to mice treated with DMSO.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The contents of all references, patents and published patent applications cited throughout this application are incorporated herein by reference in their entirety, particularly for the use or subject matter referenced herein.

We claim:

1. A method for treating a cancer selected from colon cancer, rectal cancer, breast cancer, and lung cancer in a subject, the method comprising:
    administering to a subject in need of such treatment a therapeutically effective amount of myrsinoic acid A or a pharmaceutically acceptable salt thereof, to treat the cancer in the subject.

2. The method of claim 1, wherein treatment suppresses further growth of the cancer.

3. The method of claim 1, wherein treatment results in regression of the cancer.

4. The method of claim 1, wherein the cancer is characterized by cells having increased Epidermal Growth Factor Receptor signaling.

5. The method of claim 1, wherein the subject is otherwise free of symptoms treatable by myrsinoic acid A, or a pharmaceutically acceptable salt thereof.

6. A method for suppressing the growth of a cell selected from a colon cancer cell, a rectal cancer cell, a breast cancer cell, and a lung cancer cell, the method comprising: contacting the cell with a composition comprising myrsinoic acid A, or a pharmaceutically acceptable salt thereof, to suppress the growth of the cell.

7. The method of claim 6, wherein the cell has an increased Epidermal Growth Factor Receptor signaling.

8. The method of claim 1, wherein the cancer is colon cancer.

9. The method of claim 1, wherein the cancer is rectal cancer.

10. The method of claim 1, wherein the cancer is breast cancer.

11. The method of claim 1, wherein the cancer is lung cancer.

12. A method for treating a cancer characterized by cells having increased Epidermal Growth Factor Receptor signaling in a subject in need thereof, wherein said cancer is selected from colon cancer, rectal cancer, breast cancer, and lung cancer, the method comprising:
    identifying the cells of the cancer as having increased Epidermal Growth Factor Receptor signaling as compared to wild-type cells; and
    if said cells are identified, administering to said subject a therapeutically effective amount of myrsinoic acid A, or a pharmaceutically acceptable salt thereof.

13. The method of claim 12, wherein the cancer is colon cancer.

14. The method of claim 12, wherein the cancer is rectal cancer.

15. The method of claim 12, wherein the cancer is breast cancer.

16. The method of claim 12, wherein the cancer is lung cancer.

* * * * *

UNITED STATES PATENT AND TRADEMARK OFFICE
CERTIFICATE OF CORRECTION

PATENT NO. : 8,232,318 B2  
APPLICATION NO. : 12/847509  
DATED : July 31, 2012  
INVENTOR(S) : Sam W. Lee and Anna Mandinova Page 1 of 1

It is certified that error appears in the above-identified patent and that said Letters Patent is hereby corrected as shown below:

Col. 26, Line 8, Claim 1; delete "acid A or" and insert -- acid A, or --.

Signed and Sealed this  
Sixteenth Day of October, 2012

David J. Kappos  
*Director of the United States Patent and Trademark Office*